United States Patent [19]

Polukhina et al.

[11] 4,041,375
[45] Aug. 9, 1977

[54] APPARATUS FOR MEASURING CONTENT OF MOVING DIELECTRIC MATERIALS MOISTURE

[76] Inventors: Ljudmila Alexeevna Polukhina; Vladimir Nikolaevich Polukhin, both of ulitsa Shishkova, 7, korpus 3, kv. 44; Anna Georgievna Kochetkova, mikroraion Novye Scherbinki, 28, kv. 58, all of Gorky, U.S.S.R.

[21] Appl. No.: 551,680

[22] Filed: Feb. 21, 1975

[30] Foreign Application Priority Data

Apr. 18, 1974 U.S.S.R. .............................. 2018940

[51] Int. Cl.² .................. G01R 5/28; G01R 31/02
[52] U.S. Cl. ................................. 324/32; 324/72; 324/109; 324/123 R
[58] Field of Search ............... 324/32, 72, 109, 123, 324/124; 34/1

[56] References Cited

U.S. PATENT DOCUMENTS

| | | | |
|---|---|---|---|
| 3,358,378 | 12/1967 | Downs ............................ | 34/1 |
| 3,364,423 | 1/1968 | Moulton ......................... | 324/72 |
| 3,601,694 | 8/1971 | Checketts ....................... | 324/32 |
| 3,667,036 | 5/1972 | Seachman ...................... | 324/72 |
| 3,753,102 | 8/1973 | Beck .............................. | 324/109 |
| 3,753,117 | 8/1973 | Downing et al. ................ | 325/364 |
| 3,774,110 | 11/1973 | Roueti ............................ | 324/133 |
| 3,828,256 | 8/1974 | Liu ................................. | 324/133 |
| 3,867,695 | 2/1975 | Lay, Jr. et al. ................. | 324/123 R |

Primary Examiner—Rudolph V. Rolinec
Assistant Examiner—Vincent J. Sunderdick

[57] ABSTRACT

The apparatus is intended for measuring the moisture content of moving dielectric materials. The apparatus comprises an aerial adapted to directly receive electromagnetic radiation signals caused by static electric discharges occurring at each moment of time between production apparatus and a moving dielectric material, the signals carrying information about the moisture content of the material. The aerial is connected to a bandpass tuned filter, a detector, an inverter and a recording device, all of which are connected in series. The apparatus may be provided with one or two comparators to prevent the occurrence of a false signal when the moving material breaks up and to register overloading of the device.

2 Claims, 3 Drawing Figures

APPARATUS FOR MEASURING CONTENT OF MOVING DIELECTRIC MATERIALS MOISTURE

BACKGROUND OF THE INVENTION

The present invention relates to apparatus for measuring the physical properties of dielectric materials, and, more particularly, it relates to apparatus for measuring the moisture content of moving dielectric materials, such as a paper web, woven cloth, etc.

There exists apparatuses for measuring the moisture content of moving dielectric materials, e.g. of a moving paper web, having their operation based on determining the intensity of the electromagnetic radiation created by electric discharges occuring between the moving paper web and the associated machinery on account of adhesion and friction therebetween.

These apparatuses of the prior art comprise means adapted to receive directly the electric signals carrying information representative of the moisture content of the moving dielectric material and to transmit these signals to electric measuring systems for converting the values of these signals into values proportional to the moisture content of the moving dielectric material.

The abovementioned means in the known apparatus includes serials adapted to receive the electromagnetic field or radiation, whereas the electric measuring system includes a band-pass tuned filter, an amplifier, a detector and a registering device, connected in series.

The apparatus of the prior art is equipped with an inverted scale wherein the zero reading is at the extreme right, which complicates the recording of the readings, since the readings are to be calculated from the right to the left when the apparatus is operated in a registration mode. Furthermore, the known apparatus cannot be incorporated in an automatic control system, both on account of its inverted scale and of its propensity to produce a false signal should the moving material break. In such a case, when actually the material is not advanced, the pointer of the registering device is in its extreme left position which is an indication of a maximum moisture content, e.g. of the necessity to add steam to the drying unit, whereas in fact it is necessary to reduce the steam supply.

Moreover, to ensure normal operation of the apparatus, both when it is operated in a registration mode and when it is incorporated in an automatic control system, there should be provided registration of an overload condition of the registering device, should an excessively great signal be applied to the input of the apparatus.

SUMMARY OF THE INVENTION

It is an object of the present invention to create an apparatus for measuring the moisture content of moving dielectric materials, e.g. of a moving paper web, having a direct reading scale with the zero reading at the extreme left and incorporating means for registering overloading of the apparatus, to improve the conditions of operating same and to provide for incorporation thereof into systems of automatic control of the moisture content of moving dielectric materials.

This and other objects are attained in an apparatus for measuring the moisture content of moving dielectric materials, e.g. of a moving paper web, comprising an aerial adapted to receive directly the signals coming from an electromagnetic field irradiated by discharges occuring between the moving dlelectric material and the associated production equipment contacted thereby, owing to adhesion and friction therebetween, the signals carrying information representative of the moisture content of the material, the aerial being connected to an electronic measuring system including a tuned band-pass filter, a detector and a registering device. The apparatus, in accordance with the present invention, additionally includes an invertor connected to the output of the detector and electrically connected to the input of the registering device.

It is preferred, in order to preclude occurrence of a false signal upon breakage of the moving material, that the apparatus should be additionally provided with a comparator means including a series connection of a zero or null circuit and a transistor triode. The zero circuit is connected to the output of the detector and the transistor triode has its collector connected to the output of the inverter and its emitter connected to the input of the registering device.

To ensure registering of overload conditions of the apparatus, it is preferred that the apparatus should include a second comparator including a series connection of a zero circuit and a transistor triode, and a pilot lamp, the zero circuit being connected to the input of the invertor and the transistor having its collector connected to the pilot lamp.

An apparatus for measuring the moisture content of moving dielectric materials having the herein disclosed structure offers a direct reading scale, i.e. when the moisture content or the moving dielectric material increases, the reading of the registering device increases accordingly, with the pointer of the device moving from the left to the right, which is convenient for the operator.

The incorporation in the apparatus of the two comparators allows the apparatus to be employed in automatic control systems, owing to the following advantageous features: firstly, when the apparatus for measuring the moisture content of moving materials is connected to the mains supply, and there is no signal at the input of the aerial thereof, the pointer of the apparatus rests in its zero reading position at the extreme left; secondly, should there occur breakage of the moving material, the registering device is positively disabled, whereby generation of a false signal allegedly indicative or the presence of a very moist material is precluded, which would have normally set the system of automatic moisture content control to raise the temperature of the drying facilities, e.g. of the drying cylinders. Whereas there is in fact no moving dielectric material present, and the temperature of the drying cylinders is to be reduced.

Furthermore, there is provided means for registering and monitoring possible overloading of the device, which is likewise essential for the selection of an optimal operating duty of the apparatus, both wnen the latter is operated in a registering mode and when it is incorporated in a system of automatic control of the moisture content of a moving dielectric material.

Under production conditions control of the moisture content of a moving dielectric material not only provides for improving the quality of the final product, but also enhances material and energy savings.

BRIEF DESCRIPTION OF THE DRAWINGS

The present invention will be better understood from the following description of embodiments thereof, with reference being made to the accompanying drawings, wherein.

DETAILED DESCRIPTION OF THE PREFERRED EMBODIMENTS

In the disclosure to follow hereinbelow there will be described modification of an apparatus for measuring the moisture content of moving dielectric materials, embodying the invention, the material being in the form of a moving paper web 1.

Figure 1:
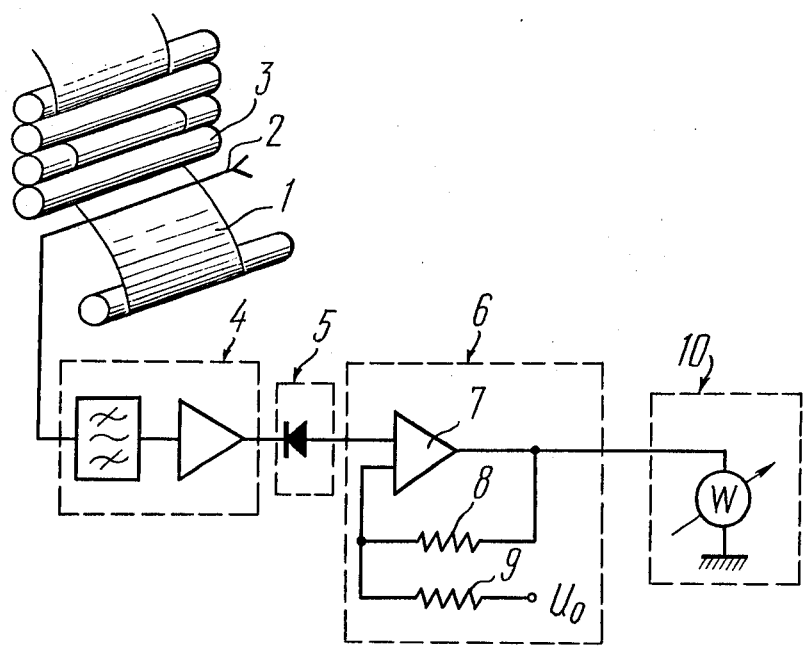
FIG. 1 shows the circuit diagram of an apparatus for measuring the moisture content of moving dielectric materials in accordance with the present invention, also showing schematically the moving dielectric material and the rolls of the associated production equipment.

The apparatus schematically illustrated in FIG. 1 comprises an aerial 2 adapted to receive directly an electromagnetic radiation field. The source of this electromagnetic radiation are static electricity discharges. This static electricity having a magnitude high enough to produce such discharges is originated by adhesion and friction between the moving paper web 1 and the associated production equipment, e.g. the bottom roll 3 of the calender roll battery of a paper-making machine. The dryer that the paper web 1, is the greater voltage will be produced between the paper web 1 and the bottom roll 3 of the calendar battery of the paper-making machine as the web moves off this roll. Quite obviously, greater voltage values produce discharges of greater power, manifesting themselves by a greater intensity of the electromagnetic field, and, consequently, the magnitude of the signal received by the aerial 2 is greater. On the other hand, more moist paper web 1 sends a weaker signal to the aerial 2. The signal received by the aerial 2 is fed to the electronic measuring system.

The electronic measuring system includes a serial electric connection of a tuned band-pass filter 4, a detector circuit 5, an invertor circuit 6 including an operational amplifier 7 with a feedback connection provided by a resistor 8. One of the inputs of the amplifier 7 has fed thereto a signal coming from the output of the detector circuit 5, while the other input thereof is supplied with a preselected reference voltage $U_o$ through a resistor 9. The system also includes a registering device 10 which in the presently described embodiment is a combination of a microammeter and a chart recorder calibrated in moisture content units.

The apparatus illustrated in FIG. 2 differs from the one described hereinabove in that it additionally includes a comparator circuit 11 incorporating a zero circuit 12 and a transistor triode 13, the zero circuit 12 being connected to the output of the detector 5 and the transistor 13 having the collector thereof connected to the output of the invertor circuit 6, while the emitter thereof is connected through a resistor 14 to the input of the registering device 10. The zero circuit 12 in the present embodiment is an operational amplifier having one input thereof supplied with the signal coming from the output of the detector 5 and the other input thereof supplied with a preselected permanent voltage $U_1$.

Another modification of the herein disclosed apparatus, illustrated in FIG. 3 of the appended drawings, differs from the one described hereinabove in connection with FIG. 2 in that it includes a second comparator circuit 15 incorporating a zero circuit 16 and a transistor triode 17, connected in series, and a pilot lamp 18, the zero circuit 16 being connected to the output of the invertor circuit 6, the collector of the transistor 17 being connected to the pilot lamp 18 and the emitter thereof being grounded.

In the presently described embodiment the zero circuit 18 includes an operational amplifier of which one input is connected to receive the signal from the output of the invertor 6 and the other input is grounded.

The operation of the herein disclosed apparatus is as follows.

The process of measuring of the moisture content of the moving paper web 1 (FIGS. 1, 2 and 3) is based on evaluation of the intensity of the electromagnetic field created by discharges occuring between the moving paper web 1 and the associated production equipment. i.e., the bottom roll 3 of the calender roll battery of the paper-making machine, owing to adhesion and friction therebetween.

The electromagnetic waves which, as it has been discussed hereinabove, carry information representative of the moisture content of the moving paper web 1, are received by the aerial 2.

The latter feeds signals to the band-pass tuned filter 4 which separates from the spectrum of oscillations received by the aerial 2 the signal within a predetermined frequency band. The high-frequency voltage coming from the output of the filter 4 is processed by the detector circuit 5, and the resulting signal is fed to the invertor circuit 6. The polarity of the voltage at the output of the detector 5 and of the reference voltage $U_o$, as well as the mode of supplying these voltages to the operational amplifier 7 of the invertor 6, operating in the mode of a scaling amplifier, are such that the signal coming from the detector circuit 5 will be inverted. In other words, the invertor circuit 6 performs the following function:

$$U_2 = k(1 - \frac{U_3}{U_o}),$$

where
  $U_2$ is the voltage across the output of the invertor 6;
  $U_3$ is the voltage across the output of the detector 5;
  $U_o$ is the reference voltage supplied to the respective input of the operational amplifier of the invertor 6;
  $k$ is the transfer ratio of the invertor 6.

The signal produced at the output of the invertor 6 is directly related to the moisture content of the moving web, because the voltage $U_3$ across the output of the detector 5 and the moisture content of the paper web 1 are related, as follows;

$$U_3 = U_{max}(1 - W),$$

where
  $U_3$ is the voltage across the output of the detector 5;
  $U_{max}$ is the maximum voltage across the output of the detector 5, when the moisture content of the paper web approaches 0 ( zero );
  W is the moisture content of the paper web.

Figure 2:
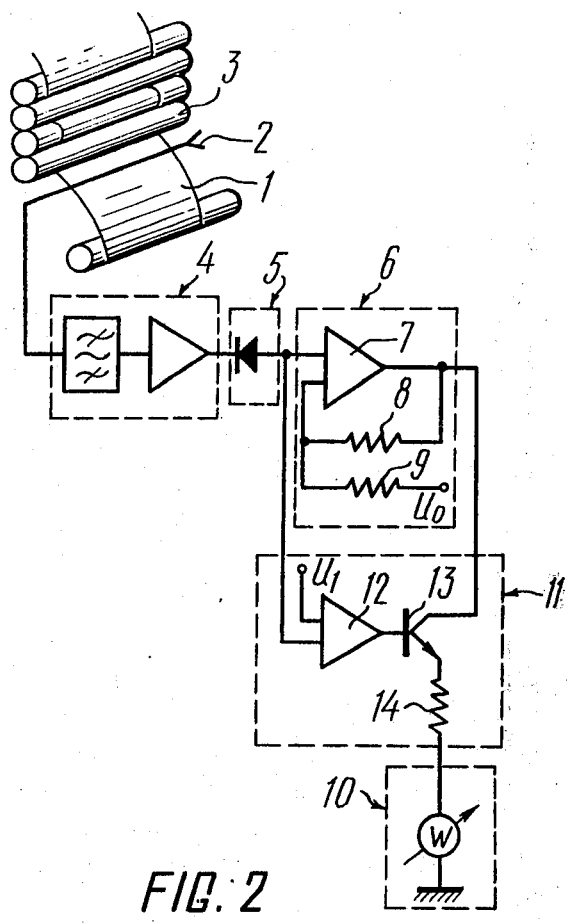
FIG. 2 is a circuit diagram of a similar apparatus in accodance with the invention, additionally including a single comparator.

The invertor 6 of the apparatus illustrated in FIG. 2 feeds a signal proportional to the moisture content of the paper web to the collector of the transistor triode 13 of the comparison circuit or comparator 11. The zero circuit of the comparator 11 is connected so that when the voltage coming from the output of the detector 5 is lower than the preselected reference voltage $U_1$, there is produced a signal opening the transistor 13, whereby the signal from the output of the invertor 6 is supplied through the transistor 13 to the registering device 10; otherwise, should the voltage across the output of the detector 5 exceed the reference voltage $U_1$ corresponding to the absence of a signal at the input of the aerial 2, there is produced a signal disabling the transistor 13, whereby the signal coming from the output of the invertor 6 fails to pass through the transistor 13, and the registering device 10 is disconnected from the system, i.e., the pointer of the registering device 10 remains at the zero mark.

Figure 3:
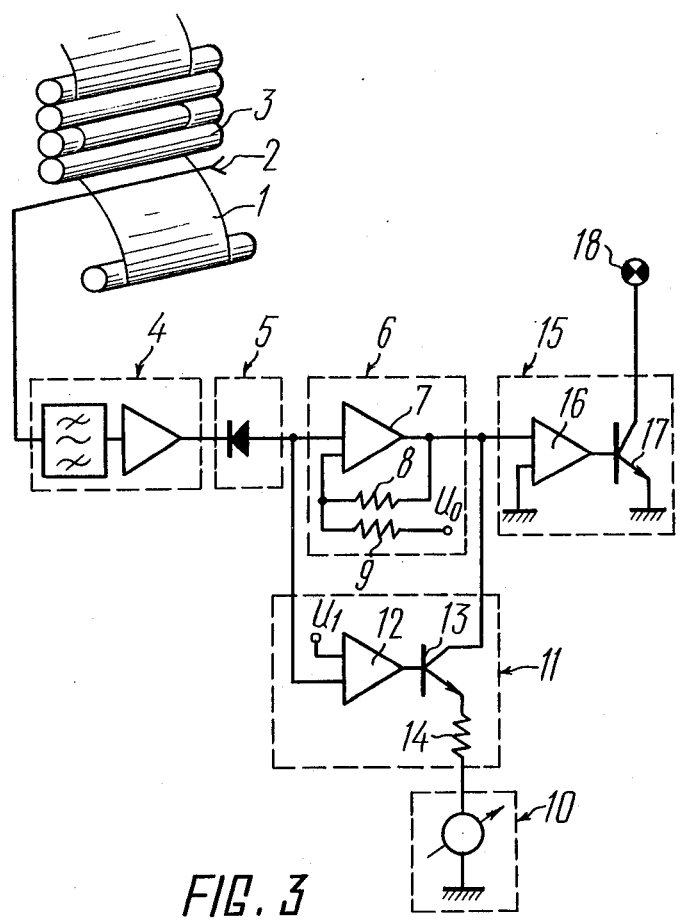
FIG. 3 is the circuit diagram of a similar apparatus in accordance with the invention, including two comparators.

In the apparatus illustrated in FIG. 3 the signal at the output of the invertor 6, proportional to the moisture content W of the paper web 1, is additionally supplied to the input of the zero circuit 16 of the comparison circuit or comparator 15.

When the voltage at the output of the invertor 6 is within a range corresponding to the working range of the signals at the input of the aerial 2, this voltage supplied to one input of the zero circuit 16 of which the other input is grounded results in a signal of negative polarity being sent to disable the transistor 17, whereby the pilot lamp 18 does not light. Should the signal at the input of the aerial 2 exceed the abovementioned range, the signal at the output of the invertor 6 changes its sense with respect to the body of the apparatus (i.e., to ground), whereby the transistor 17 is opened, and the pilot lamp 18 lights to indicate that the apparatus is overloaded, the pointer of the registering device 10 being simultaneously driven toward the maximum moisture content reading.

The herein disclosed apparatus for measuring the moisture content of moving dielectric material offers a direct reading scale of the moisture content values, as well as monitoring the overloading of the apparatus.

The apparatus of the herein disclosed structure has been found to measure the moisture content with high accuracy, as high as ± 0.1% moisture, to be reliable and convenient in operation.

Moreover, such apparatus can be incorporated in systems effecting automatic control of the moisture content of moving dielectric materials.

What we claim is:

1. An apparatus for measuring the moisture content of moving dielectric materials, comprising: an aerial provided to receive directly electromagnetic signals irradiated by discharges of static electricity occurring at each moment of time between a production apparatus and the moving dielectric material and carrying information about the moisture content of said material; a band-pass tuned filter connected to said aerial; a detector circuit connected to receive an output of said filter; an inverter connected to receive an output of said detector circuit; and a registering device connected electrically with an output of said inverter circuit; a first comparator means, said first comparator means including a zero circuit connected to the output of said detector circuit; said comparator means further including a transistor triode, the base of which is connected to an output of said zero circuit; the collector of said transistor triode being connected to an output of said detector circuit and the emitter of said transistor triode being connected to said registering device.

2. The apparatus of claim 1 wherein there is further included a second comparator means comprising a second zero circuit connected to the output of said inverter circuit; a transistor triode the base of which is connected to an output of said second comparator zero circuit; the collector of said second comparator transistor triode is connected to a pilot lamp and the emitter of said second comparator transistor triode is grounded.

* * * * *